(12) United States Patent
Hirano

(10) Patent No.: US 6,582,361 B2
(45) Date of Patent: Jun. 24, 2003

(54) WATERTIGHT CAP FOR ENDOSCOPE

(75) Inventor: Sota Hirano, Saitama (JP)

(73) Assignee: Fuji Photo Optical Co., Ltd., Saitama (JP)

( * ) Notice: Subject to any disclaimer, the term of this patent is extended or adjusted under 35 U.S.C. 154(b) by 105 days.

(21) Appl. No.: 09/960,926

(22) Filed: Sep. 25, 2001

(65) Prior Publication Data

US 2002/0040180 A1 Apr. 4, 2002

(30) Foreign Application Priority Data

Sep. 29, 2000 (JP) ........................................ 2000-298675

(51) Int. Cl.7 ................................................. A61B 1/00
(52) U.S. Cl. ........................................ 600/132; 600/133
(58) Field of Search ............................... 600/133, 132, 600/154, 155; 215/246, 307, 310

(56) References Cited

U.S. PATENT DOCUMENTS

| | | | | |
|---|---|---|---|---|
| 4,241,729 A | * | 12/1980 | Aoshiro | 600/133 |
| 4,574,783 A | * | 3/1986 | Kazuhiro et al. | 600/112 |
| 5,588,950 A | * | 12/1996 | Sano et al. | 600/178 |
| 5,611,769 A | * | 3/1997 | Monroe | 600/112 |
| 5,868,667 A | * | 2/1999 | Lin et al. | 600/133 |
| 6,491,625 B1 | * | 12/2002 | Newton et al. | 600/133 |
| 6,502,976 B1 | * | 1/2003 | Bernhard | 362/555 |
| 6,510,277 B1 | * | 1/2003 | Dongo | 385/147 |
| 6,514,198 B2 | * | 2/2003 | Ishibiki | 600/133 |
| 2002/0115907 A1 | * | 8/2002 | Mitsumori | 600/131 |
| 2002/0128535 A1 | * | 9/2002 | Kikuchi et al. | 600/101 |

* cited by examiner

Primary Examiner—Linda C. M. Dvorak
Assistant Examiner—Jocelyn Ram
(74) Attorney, Agent, or Firm—Oliff & Berridge, PLC

(57) ABSTRACT

When washing the electronic endoscope, a cleaning liquid that has flowed into a space between a shell of an electric connector and an external cylinder of a watertight cap does not reach a connector pin that resides inside the shell since an O-ring seals an internal cylinder of the watertight cap and the shell. The cleaning liquid is discharged to the outside of the watertight cap through discharge holes, which are formed between the external cylinder and the internal cylinder.

2 Claims, 4 Drawing Sheets

WATERTIGHT CAP FOR ENDOSCOPE

BACKGROUND OF THE INVENTION

1. Field of the Invention

The present invention relates to a watertight cap which is attached to an electric connector of an electronic endoscope so as to make the electric connector watertight in order to prevent a cleaning liquid from entering when cleaning the electronic endoscope.

2. Description of the Related Art

An electronic endoscope for medical use has a solid-state imaging device, which is arranged at the distal end of the insertion part and is connected to an electric connector through a multi-cored cable. The electric connector is provided at the end of a flexible cable, which is extended from a hand control part of the endoscope. A subject image which is captured through the solid-state imaging device is displayed on a monitor by connecting the electric connector with an image processing device called a processor.

The endoscope is immersed in a cleaning liquid after every use in order to be cleaned, but because the electronic endoscope has the electric connector, the electronic endoscope is cleaned while a watertight cap is attached on the electric connector.

FIG. 7 is a semi-section view showing a conventional watertight cap 1 being attached to an electric connector 2. The watertight cap 1 has a click ball 4 and an O-ring 5 provided to a cylindrical part 3, which is pushed into a space between a shell 6 and a release sleeve 7 of the electric connector 1, whereby the click ball 4 engages with a receding part 8, which is formed on an outer periphery of the shell 6. A that time, the watertight cap 1 is watertightly attached on the electric connector 2 by pressing the O-ring 5 against the outer periphery of the shell 6. Connector pins 2A of the electric connector 2 are thus prevented by the watertight cap 1 from getting wet with the cleaning liquid, and the electronic endoscope is cleaned in that state.

However, the conventional watertight cap 1 still has a problem in that the connector pins 2A may get wet with the cleaning liquid when detaching the watertight cap 1 from the electric connector 2. This problem occurs for the following reason. In the structure of the watertight cap 1, it is difficult to discharge the cleaning liquid flowing into the space 9 between the cylindrical part 3 and the shell 6. While detaching the watertight cap 1, the cleaning liquid left in the space 9 follows the cylindrical part 3 and is dragged out to the end of the shell 6, then the cleaning liquid enters from the end into the inside of the shell 6 and reaches the connector pins 2A.

SUMMARY OF THE INVENTION

The present invention has been developed in view of the above-described circumstance, and has as its object the provision of a watertight cap for a connector of an endoscope which can prevent the connector pins from getting wet with a cleaning liquid at a time of detaching the watertight cap.

In order to achieve the above-described object, the present invention is directed to a watertight cap which is detachably attached to a connector of an endoscope, the watertight cap comprising: an external cylinder having an engaging part being detachably engaged with an outer periphery of a shell member provided around a connector pin of the connector; and an internal cylinder arranged inside the external cylinder, an end of the internal cylinder being closed, the internal cylinder having a seal member being pressed against an inner periphery of the shell member, wherein a discharge hole opening to outside is formed between the external cylinder and the internal cylinder when the watertight cap is attached on the connector.

According to the present invention, the cleaning liquid flows into the space between the shell member of the connector and the external cylinder but does not enter into a side of the connector pin since the internal cylinder and the shell member are sealed, and the cleaning liquid is discharged to the outside of the watertight cap through the discharge holes, which are formed between the external cylinder and the internal cylinder. Thus, the watertight cap of the present invention can prevent the connector pins from getting wet with the cleaning liquid at the time of detaching the water cap because the cleaning liquid is not left in the space between the shell member and the external cylinder.

Preferably, the shell member of the connector comprises a release sleeve arranged outside thereof for releasing an engagement between the shell member and the engaging part of the external cylinder; the external cylinder has an external form having a small diameter part except the engaging part; and a discharge passage is formed between the small diameter part and the release sleeve. Hence, the watertight cap of the present invention can discharge the cleaning liquid flowing into the space between the external cylinder and the release sleeve to the outside of the watertight cap through the discharge passage. Thus, the watertight cap can prevent the connector pin from getting wet with the cleaning liquid at the time of detaching the watertight cap.

BRIEF DESCRIPTION OF THE DRAWINGS

The nature of this invention, as well as other objects and advantages thereof will be explained in the following with reference to the accompanying drawings, in which like reference characters designate the same or similar parts throughout the figures and wherein.

DETAILED DESCRIPTION OF THE PREFERRED EMBODIMENTS

Hereunder a preferred embodiment of a watertight cap for a connector of an endoscope will be described in detail in accordance with the accompanying drawings.

Figure 1:
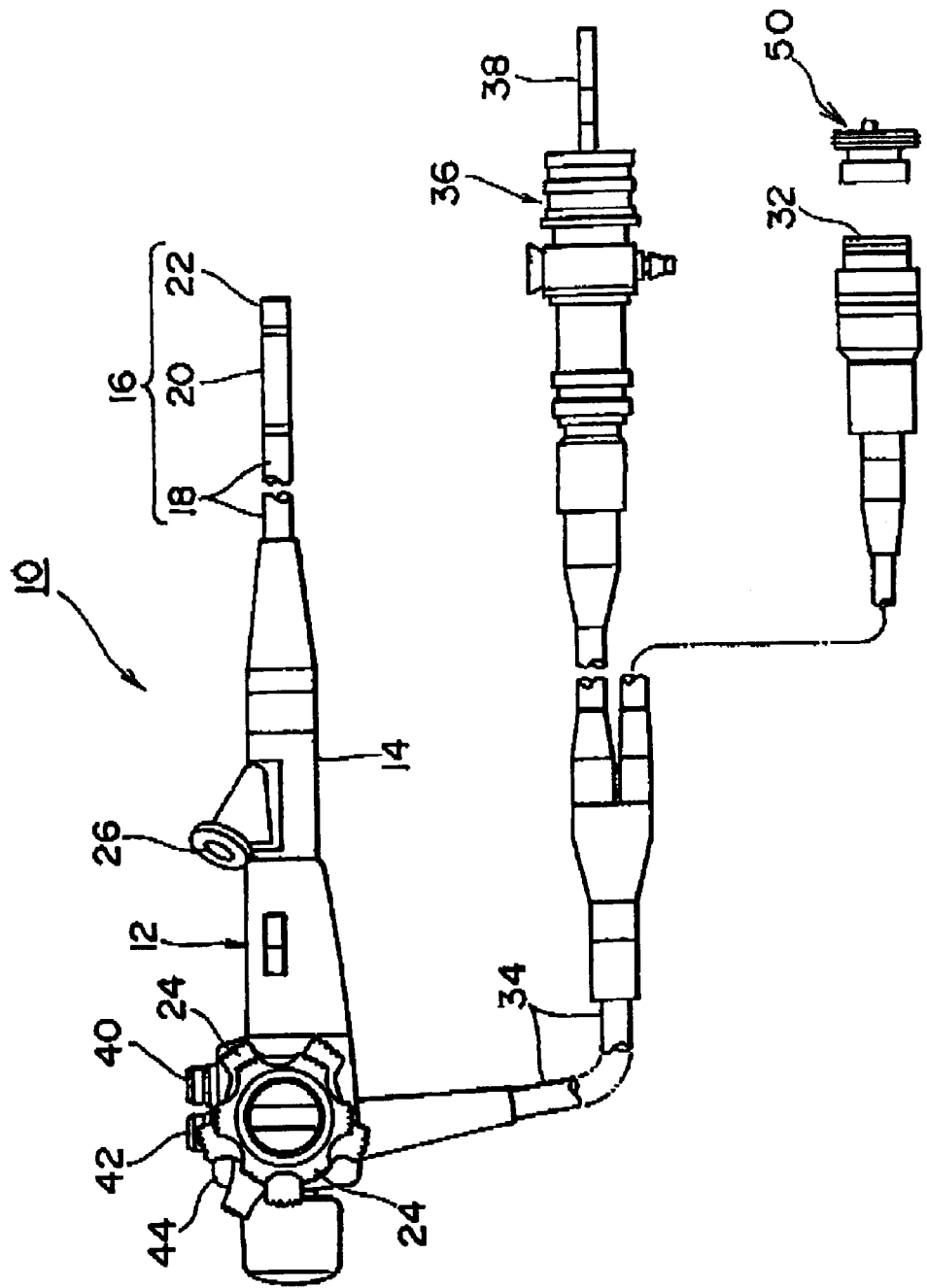
FIG. 1 is a view showing an entire electronic endoscope to which a watertight cap for a connector according to an embodiment of the present invention is attached.

FIG. 1 shows an electronic endoscope 10 to which a watertight tap 50 for a connector 32 of a present embodiment is attached. The electronic endoscope 10 is constructed of a hand control part 12, an insertion part 16, and so forth. The insertion part 16 is connected to a branched part 14 of a treatment tool inlet of the hand control part 12, and is connected of a flexible part 18, a bending part 20, and a distal end assembly 22. The bending part 20 is connected to a pair of bend control knobs 24, which are provided to the hand control part 12, through bending operation wires (not shown) arranged in the flexible part 18. Therefore, when the user rotates the bend control knobs 24, the bending part 20 is bent and the distal end assembly 22 is pointed at a desired direction. Through the treatment tool inlet 26, treatment tools such as biopsy forceps, a high-frequency snare, and so forth, are inserted into the insertion part 16.

A treatment tool insertion channel outlet (not shown) is formed on an end face of the distal end assembly 22. The treatment tool insertion channel outlet is connected to the treatment tool inlet 26 through a treatment tool insertion channel arranged in the insertion part 16. Hence, the treatment tool inserted through the treatment tool inlet 26 leads to the treatment tool insertion channel outlet, and is projected to the front from the treatment tool insertion channel outlet when used.

An object optical system, an air/water supply outlet, an illumination lens, and so forth, all not shown, are provided at the proximity of the treatment tool insertion channel outlet. An image of the observed subject captured by the object optical system is formed on an image forming surface of a solid-state imaging device (such as a CCD), which is arranged to the back of the object optical system. Core wires of a multi-cored able are connected to terminals of a board of the solid-state imaging device. The multi-cored cable is arranged through the insertion part 16, the hand control part 12 and a flexible cable 34, and is connected to an electric connector 32, which is provided to the proximal end of the flexible cable 34. The electric connector 32 is connected to a processor (not shown) and the image of the observed subject imaged by the solid-state imaging device is displayed on a monitor (not shown).

A light guide (not shown) is provided at the back of the illumination lens. The light guide is arranged through the insertion part 16, the hand control part 12 and the flexible cable 34, then is connected to a light guide stick 38 of a light guide connector, which is provided to the flexible cable 34. When the light guide stick 38 is connected to a light source device (not shown), the light from the light source device is emitted toward the subject from the illumination lens through the light guide.

The hand control part 12 is provided with an air/water supply valve 40, which is operated by the user, and at the proximity of which a suction valve 42 and a shutter button 44 are provided next to each other.

Figure 2:
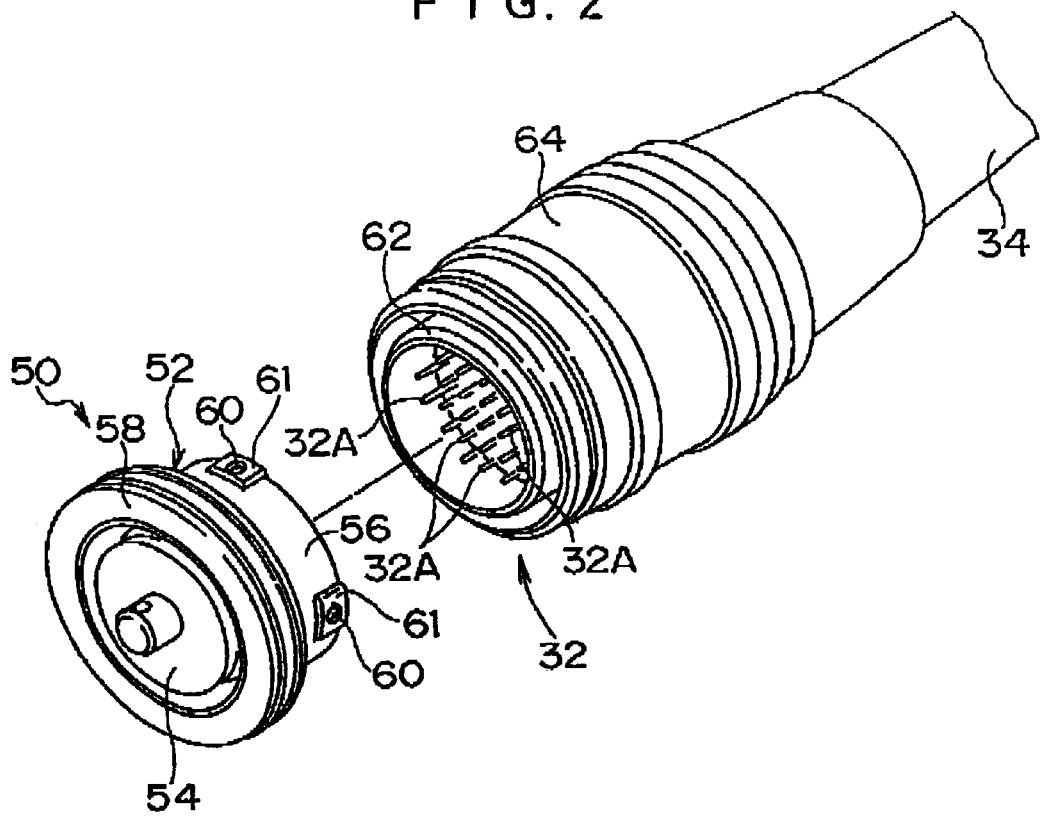
FIG. 2 is a perspective view showing an attachment between the watertight cap and an electric connector in FIG. 1.
Figure 3:
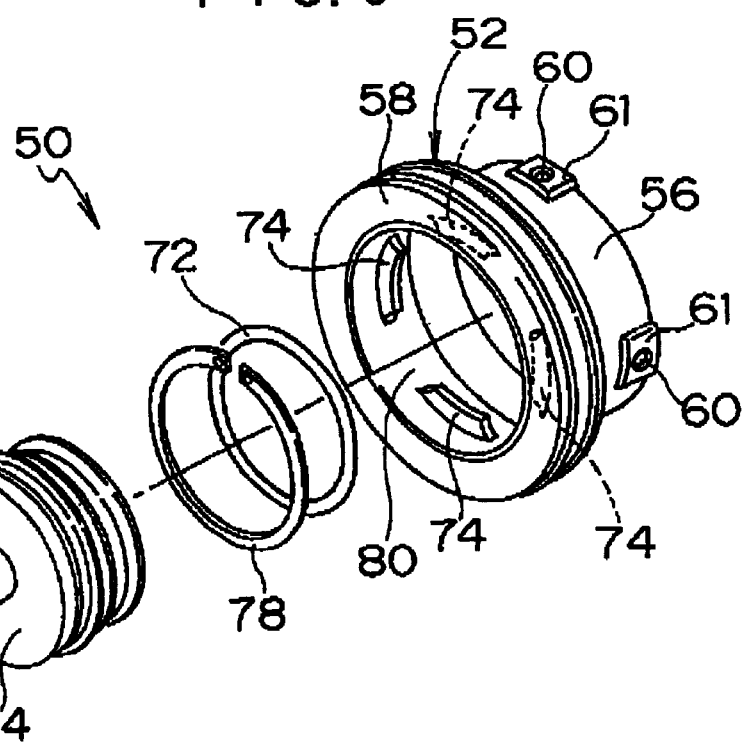
FIG. 3 is a perspective view of an assembly of the watertight cap.
Figure 4:
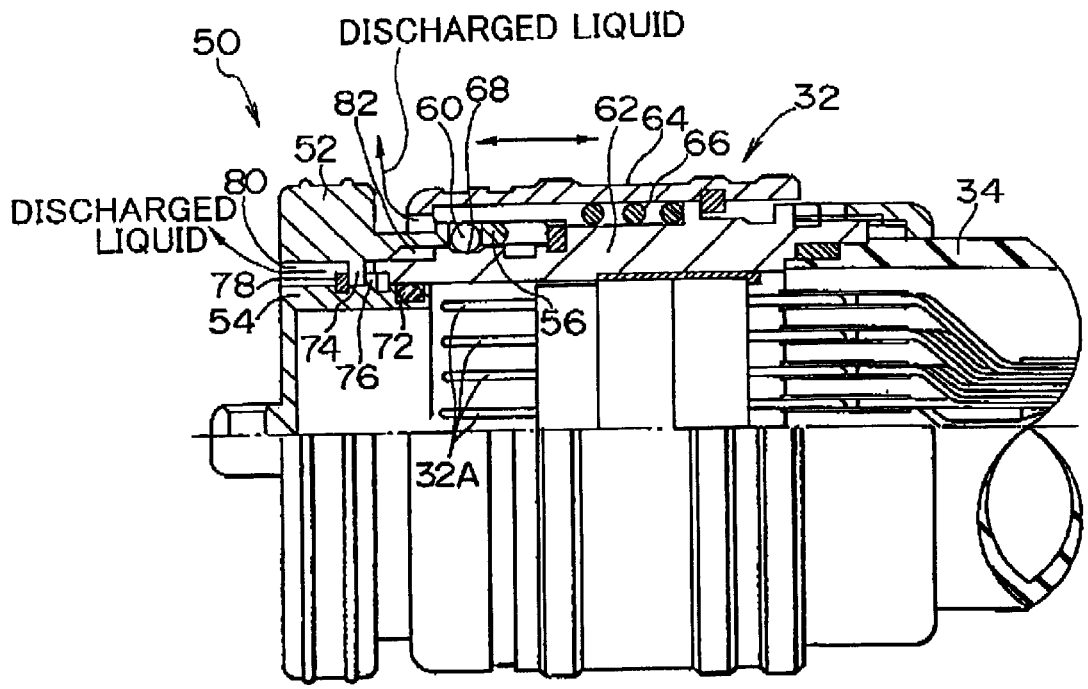
FIG. 4 is a semi-section view showing a state where the watertight cap is attached to the electric connector.

FIG. 2 shows a state before mounting the watertight cap 50 on the electric connector 32. As seen from FIGS. 2–6, the watertight cap 50 is constructed to have a double cylinder structure comprising an external cylinder 52, and an internal cylinder 54 of which end is closed.

A ring-shaped holding part 58 is formed at an end of a cylindrical part 56 of the external cylinder 52 so that the holding part 58 is formed to be the same body as the cylindrical part 56. Click balls 60 serving as engaging parts are provided at four positions on an outer periphery of the cylindrical part 56 and are provided with the same intervals as seen from FIG. 6. As seen from FIG. 4, when the cylindrical part 56 is pushed into a space between a release sleeve 64 and a shell 62 at a side of the electric connector 32, the pushing force thereby caused moves the release sleeve 64 to move to the right-hand side in FIG. 4 against the pressing force of a spring 66; consequently, the click balls 60 are engaged with a receding part 68, which is formed on an outer peripheral face of the shell 62. Even through the watertight cap 50 is pulled in an opening direction (direction to the left-hand side in FIG. 4) in that state, the watertight cap 50 cannot be pulled out of the electric connector 32 since the click balls 60 are pressed in a direction to engage with the receding part 68 by an inner peripheral face of the release sleeve 64. The watertight cap 50 is thus prevented from being pulled out of the electric connector 32. In a case where the watertight cap 50 is pulled out of the electric connector 32, the release sleeve 64 is moved to the right-hand side in FIG. 4 against the pressing force of the spring 66. The engagement of the click balls 60 with respect to the receding part 68 by the release sleeve 64 is released by that manner, and the watertight cap 50 can then be easily pulled out of the electric connector 32.

Figure 6:
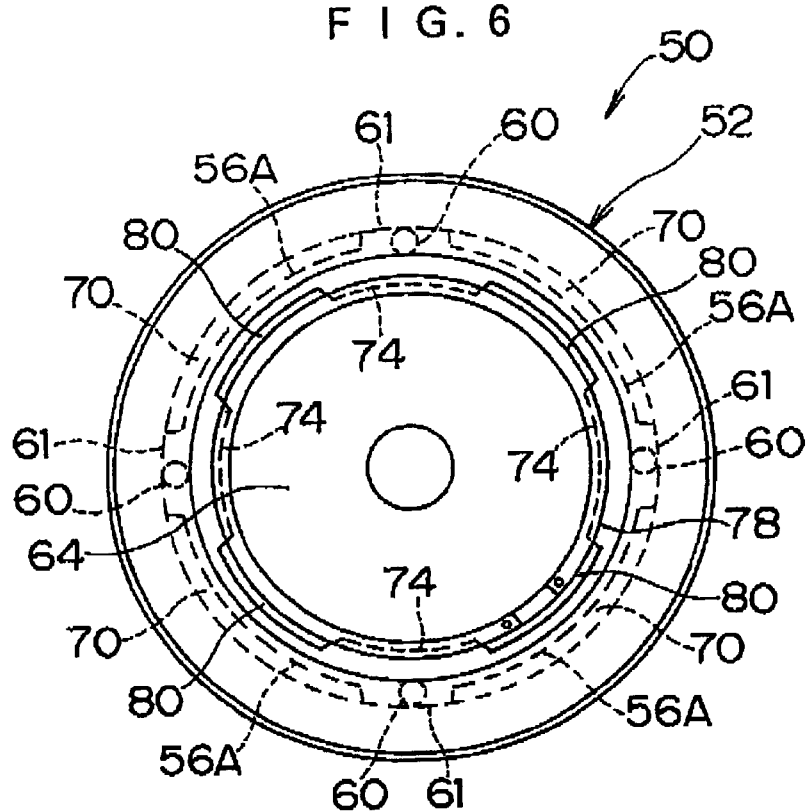
FIG. 6 is a left-hand side view along a line 6—6 of the watertight cap in FIG. 5.
Figure 7:
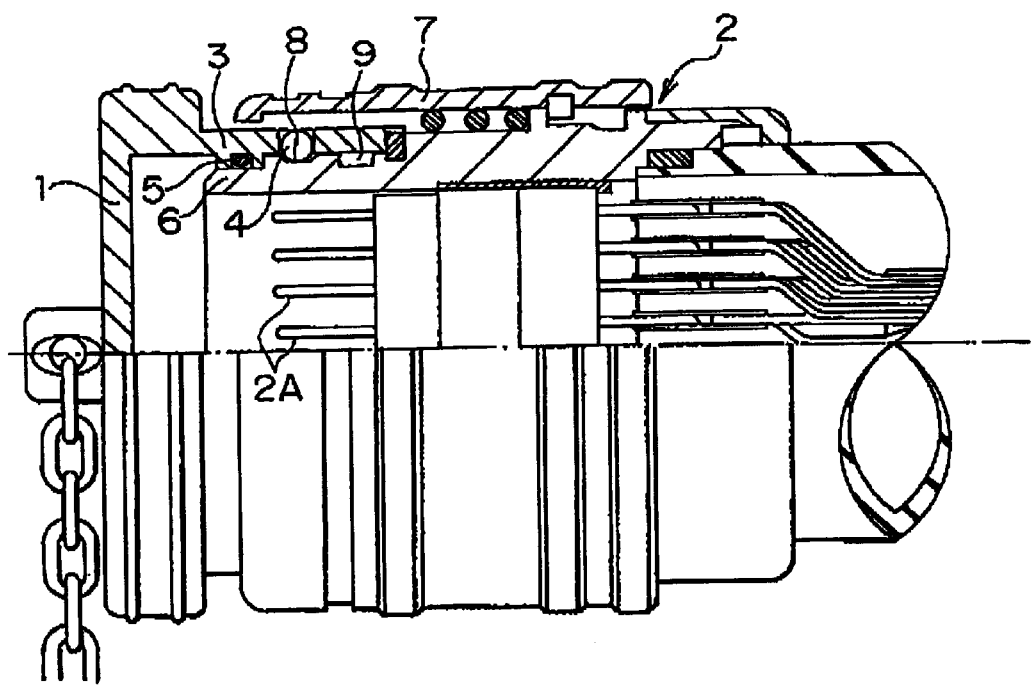
FIG. 7 is a semi-section view showing a state where a conventional watertight cap is attached to an electric connector.

As seen from FIGS. 2 and 6, the click balls 60 are provided to a mounting part 61, which projects from an outer periphery of the cylindrical part 56. The outer periphery of the cylindrical part 56 is formed to have a small diameter except the mounting part 61, and four discharge passages 70 are formed between a small diameter part 56A (see FIG. 6) and the release sleeve 64.

Figure 5:
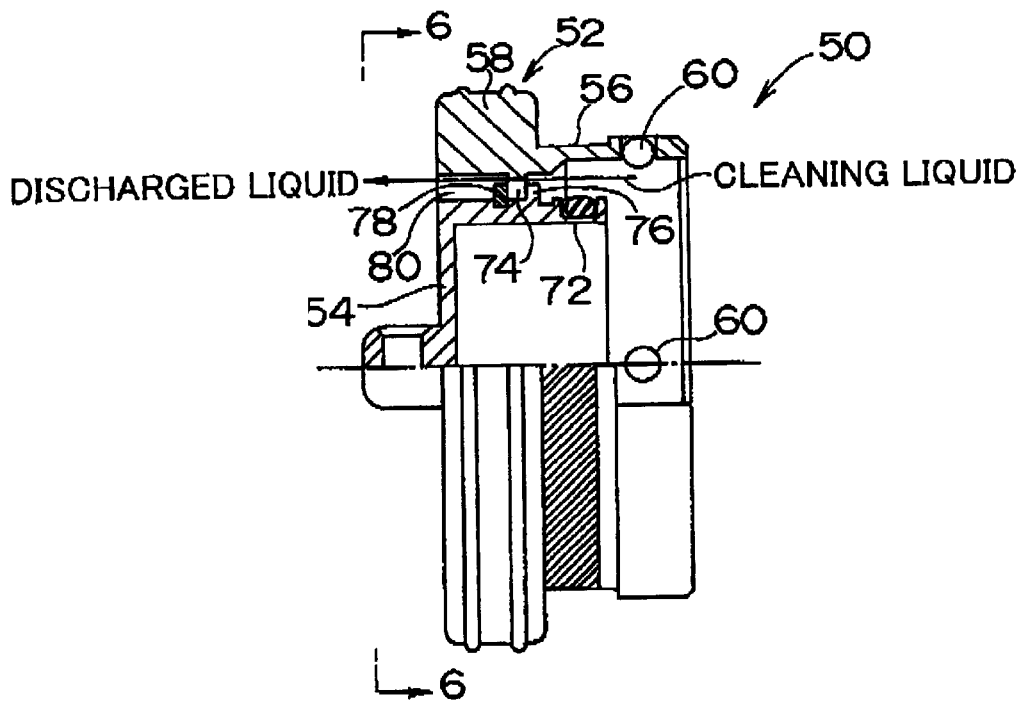
FIG. 5 is a semi-section view of the watertight cap.

Regarding now to the internal cylinder 54, an O-ring 72 is coupled on the outer periphery at the tight-hand side in FIG. 5 of an open side of the internal cylinder 54 as shown in FIG. 5. Also as seen from FIG. 4, the O-ring 72 is pressed on an inner peripheral face of the shell 62 when the watertight cap 50 is mounted on the electric connector 32. Since the internal cylinder 54 and the shell 62 are scaled with the O-ring 72 in that manner, the cleaning liquid is prevented from entering into the shell 62, that is, the side of the connector pins 32A at the time of cleaning.

The external cylinder 52 and the internal cylinder 54 are connected to each other by pressing and holding four claws 74 with a C-shaped ring 78 and a projecting ridge 76, which is formed on the outer peripheral face of the internal cylinder 54. The four claws 74 are provided on the inner peripheral face of the external cylinder 52 in FIG. 3 with the same intervals. In the connecting structure, discharge holes 80 connected to the outside are formed between the external cylinder 52 and the internal cylinder 54 in the manner shown in FIG. 6. The discharge holes 80 are formed by the three parts the inner peripheral face of the external cylinder 52, sides of opposing two of the claws 74, and an outer peripheral face of the C-shaped ring 78.

Now, an operation of the watertight cap 50 will be described.

At the time of cleaning the electronic endoscope 10, the cleaning liquid flowing into a space 82 (refer to FIG. 4) between the shell 62 of the electric connector 32 and the external cylinder 52 of the watertight cap 50 does not enter into the side of the connector pins 32A, which is the inside of the shell 62, since the internal cylinder 54 of the watertight cap 50 and the shell 62 are sealed by the O-ring 72. The cleaning liquid flowing into the space 82 is discharged to the outside of the watertight cap 50 through the discharge holes 80, which are formed between the external cylinder 52 and the internal cylinder 54 (see FIGS. 4 and 5).

According to the watertight cap 50 of the present embodiment, the cleaning liquid is not left in the space 82, and thus the connector pins 32 can be prevented from getting wet with the cleaning liquid at the time of detaching the watertight cap 50.

Moreover, according to the watertight cap 50, a part except the mounting part 61 of the click balls 60 is formed to have the small diameter, and the discharge passages 70 are formed between the small diameter part 56A (refer to FIG. 6) and the release sleeve 64. Hence, the watertight cap 50 can discharge the cleaning liquid that has flowed into the space between the external cylinder 52 and the release sleeve 64 to the outside of the watertight cap 50 through the discharge passages 70 (see FIG. 4). The connector pins 32A arm thus prevented from getting wet with the cleaning liquid at the time of detaching the watertight cap 50.

As described hereinabove, according to the watertight cap for the connector of the endoscope of the present invention, the cleaning liquid flowing into a space between the shell member of the connector and the eternal cylinder of the watertight cap is discharged to the outside of the watertight cap through the discharge holes, which are formed between the external cylinder and the internal cylinder, hence the connector pin is prevented from wet with the cleaning liquid at the time of detaching the watertight cap.

Further, according to the present invention, the watertight cap of the present invention uses the electric connector in which the release sleeve is mounted on the outside of the shell member; and a part of the outer periphery of the external cylinder of the watertight cap is formed to have a small diameter except the engaging part; moreover a passage for discharging the cleaning liquid is formed between the small diameter part and the release sleeve. Therefore, the cleaning liquid flowing into a space between the external cylinder and the release sleeve is discharged to the outside of the watertight cap through the discharge passage, and the connector pin can be prevented from getting wet with the cleaning liquid at the time of detaching the watertight cap.

It should be understood, however, that there is no intention to limit the invention to the specific forms disclosed, but on the contrary, the invention is to cover all modifications, alternate constructions and equivalents falling within the spirit and scope of the invention as expressed in the appended claims.

What is claimed is:

1. A watertight cap which is detachably attached to a connector of an endoscope, the watertight cap comprising:

an external cylinder having an engaging part being detachably engaged with an outer periphery of a shell member provided around a connector pin of the connector; and an internal cylinder arranged inside the external cylinder, an end of the internal cylinder being closed, the internal cylinder having a seal member being pressed against an inner periphery of the shell member, wherein a discharge hole opening to outside is formed between the external cylinder and the internal cylinder when the watertight cap is attached on the connector.

2. The watertight cap as defined in claim 1, wherein:

the shell member of the connector comprises a release sleeve arranged outside thereof for releasing an engagement between the shell member and the engaging part of the external cylinder;

the external cylinder has an external form having a small diameter part except the engaging part; and a discharge passage is formed between the small diameter part and the release sleeve.

* * * * *